United States Patent
Kuno (10) Patent No.: US 10,638,240 B2
(45) Date of Patent: Apr. 28, 2020

(54) BONE CONDUCTION WAVE GENERATION DEVICE, BONE CONDUCTION WAVE GENERATION METHOD, BONE CONDUCTION WAVE GENERATION DEVICE PROGRAM, AND BONE CONDUCTION WAVE OUTPUT APPARATUS

(71) Applicant: CASIO COMPUTER CO., LTD., Shibuya-ku, Tokyo (JP)

(72) Inventor: Toshiya Kuno, Hamura (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 16/086,846

(22) PCT Filed: Jul. 26, 2017

(86) PCT No.: PCT/JP2017/027097
§ 371 (c)(1),
(2) Date: Sep. 20, 2018

(87) PCT Pub. No.: WO2018/051646
PCT Pub. Date: Mar. 22, 2018

(65) Prior Publication Data
US 2019/0052981 A1  Feb. 14, 2019

(30) Foreign Application Priority Data
Sep. 16, 2016  (JP) .................................. 2016-182120

(51) Int. Cl.
*H04R 25/00* (2006.01)
*H04R 1/10* (2006.01)
(Continued)

(52) U.S. Cl.
CPC ............ *H04R 25/606* (2013.01); *H04R 1/10* (2013.01); *H04R 3/12* (2013.01); *A61N 1/36036* (2017.08); *H04R 2460/13* (2013.01)

(58) Field of Classification Search
CPC .... H04R 3/12; H04R 25/606; H04R 2460/13; A61N 1/36036
See application file for complete search history.

(56) References Cited

U.S. PATENT DOCUMENTS

2014/0254840 A1* 9/2014 Norris .................... H04R 25/50
381/312

FOREIGN PATENT DOCUMENTS

| CN | 101111096 A | 1/2008 |
| CN | 105721973 A | 6/2016 |

(Continued)

OTHER PUBLICATIONS

International Search Report (ISR) dated Oct. 10, 2017 issued in International Application No. PCT/JP2017/027097.
(Continued)

*Primary Examiner* — Brian Ensey
(74) *Attorney, Agent, or Firm* — Holtz, Holtz & Volek PC (57) ABSTRACT

A bone conduction wave generation device includes a waveform generator which generates a first output wave and a second output wave for bone conduction. The waveform generator generates, on a basis of an input wave, the first output wave outside of an audible range and the second output wave outside of an audible range. The first output wave and the second output wave are to be combined into a composite wave having an audible beat.

10 Claims, 4 Drawing Sheets

(51) Int. Cl.
*H04R 3/12* (2006.01)
*A61N 1/36* (2006.01)

(56) References Cited

FOREIGN PATENT DOCUMENTS

| | | |
|---|---|---|
| JP | H04207400 A | 7/1992 |
| JP | 2002300700 A | 10/2002 |
| JP | 2004343302 A | 12/2004 |
| JP | 2008147732 A | 6/2008 |
| JP | 2009049959 A | 3/2009 |

OTHER PUBLICATIONS

Written Opinion dated Oct. 10, 2017 issued in International Application No. PCT/JP2017/027097.
International Preliminary Report on Patentability (IPRP) dated Mar. 19, 2019 (and English translation thereof) in counterpart International Application No. PCT/JP2017/027097.
Chinese Office Action dated Mar. 22, 2019 (and English translation thereof) issued in Chinese Application No. 201780004551.7.
Chinese Office Action dated Aug. 14, 2019 (and English translation thereof) issued in counterpart Chinese Application No. 201780004551.7.

* cited by examiner

BONE CONDUCTION WAVE GENERATION DEVICE, BONE CONDUCTION WAVE GENERATION METHOD, BONE CONDUCTION WAVE GENERATION DEVICE PROGRAM, AND BONE CONDUCTION WAVE OUTPUT APPARATUS

TECHNOLOGICAL FIELD

The present invention relates to a bone conduction wave generation device, a bone conduction wave generation method, a program for a bone conduction wave generation device, and a bone conduction wave output apparatus.

BACKGROUND ART

For example, a general headphone or earphone is worn such that a speaker portion (an output unit) which outputs sound is positioned to an ear hole.

A sound wave output from the speaker vibrates air which passes through an ear canal to vibrate (shake) a tympanic membrane.

As a result, the vibration of the tympanic membrane is transmitted to three ear ossicles (a stapes, a incus, and a malleus) and further to a cochlea, which is at the inner part of the ear ossicles.

The vibration received by the cochlea vibrates the lymph in the cochlea to stimulate hair cells. The stimulation is converted to an electric signal by the hair cells and transmitted to spiral ganglion cells in the cochlea. The electric signal is further transmitted to the cerebrum through vestibulocochlear nerves, so that sound can be recognized.

However, because the headphone or earphone of this kind plugs the ear hole and makes it difficult to recognize external sound, it may be dangerous to use it while walking.

Alternatively, a bone conduction speaker (an output unit) is known which does not plug the ear hole (see Patent Document 1)

Specifically, the bone conduction speaker transfers the vibration of sound directly to the cochlea through the skull.

Thus, it is not necessary to plug the ear hole, provided that the bone conduction speaker is worn at a position where vibration of a sound wave can be transferred directly to the cochlea through bones.

Thus, because it is possible to hear external sound, there is an advantage that it can be safely used even while walking.

There is also an advantage that a person having difficulty in hearing due to troubles as to tympanic membranes or ear ossicles can hear sound, provided that cochleas and auditory nerves are not damaged.

PRIOR ART DOCUMENT

Patent Document

[Patent Document 1] Japanese Patent Application Laid Open Publication No. 2008-147732

SUMMARY OF THE INVENTION

Problems to be Solved by the Invention

However, because the bone conduction speaker vibrates bones with a sound wave, it outputs a larger sound wave compared to a generally used speaker which vibrates air with a sound wave.

As a result, sound leakage from the bone conduction speaker is larger than that from a generally used speaker. Thus, there is a problem of low confidentiality regarding the output contents from the speaker.

The present invention has been made in view of the above-described circumstances. The objects of the present invention are to provide a bone conduction wave generation device, a bone conduction wave generation method, a program used in a bone conduction wave generation device, and a bone conduction wave output apparatus which have the advantage of reducing sound leakage from a bone conduction speaker (output unit).

Means for Solving the Problems

A bone conduction wave generation device according to the present invention includes a waveform generator which generates a first output wave and a second output wave for bone conduction, wherein the waveform generator generates, on a basis of an input wave, the first output wave outside of an audible range and the second output wave outside of an audible range which are to be combined into a composite wave having an audible beat.

A bone conduction wave generation method according to the present invention includes generating, on a basis of an input wave, a first output wave outside of an audible range and a second output wave outside of an audible range for bone conduction which are to be combined into a composite wave having an audible beat.

A program according to the present invention for a bone conduction wave generation device causes a bone conduction wave generation device which generates a first output wave and a second output wave for bone conduction to perform generating processing of, on a basis of an input wave, the first output wave outside of an audible range and the second output wave outside of an audible range, wherein the first output wave and the second output wave are to be combined into a composite wave having an audible beat.

A bone conduction wave output apparatus according to the present invention includes an output unit outputting a first output wave outside of an audible range for bone conduction and a second output wave outside of an audible range for bone conduction, which are to be combined into a composite wave having an audible beat, wherein the output unit includes a first output unit outputting the first output wave and a second output unit outputting the second output wave which are provided corresponding to at least one ear.

EMBODIMENTS FOR CARRYING OUT THE INVENTION

Hereinafter, a bone conduction wave output apparatus 1 according to an embodiment of the present invention will be described with reference to the attached drawings.

Figure 1:
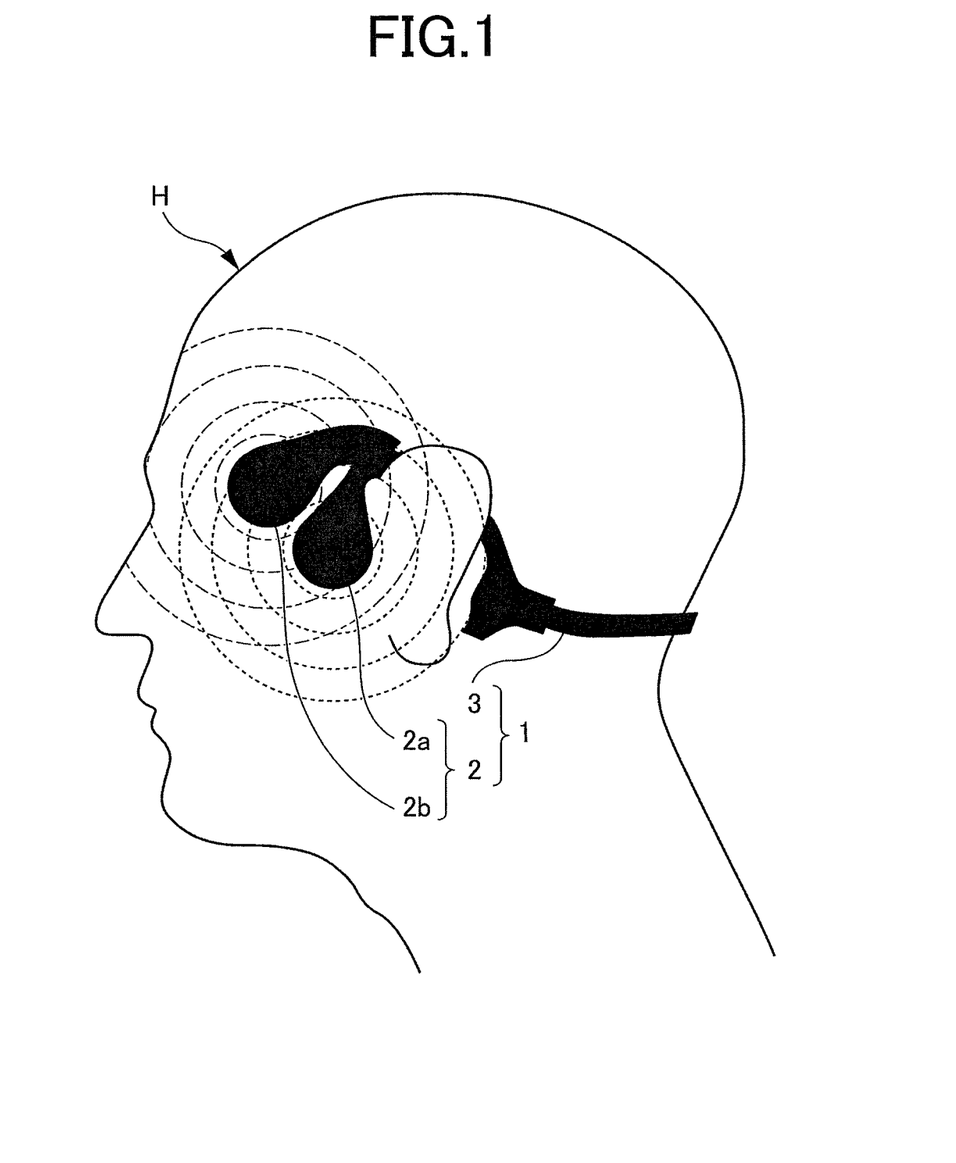
FIG. 1 is a plan view of a bone conduction wave output apparatus according to an embodiment of the present invention which is worn at a head H of a man.

FIG. 1 is a plan view showing the bone conduction wave output apparatus which is worn at a head H of a man.

(Bone Conduction Wave Output Apparatus 1)

As shown in FIG. 1, the bone conduction wave output apparatus 1 according to the embodiment is a so-called headphone type output apparatus and is provided with an output unit 2 which corresponds to one ear and which has a first output unit 2a and a second output unit 2b arranged at a predetermined distance, and an output unit 2 which corresponds to another ear at the position opposite to the side shown in FIG. 1 and which has a first output unit 2a and a second output unit 2b.

The output unit 2 provided corresponding to another ear also has the structure illustrated in FIG. 1.

The bone conduction wave output apparatus 1 has a connector 3 which connects the pair of output units 2 provided corresponding to both ears.

The connector 3 has a structure called a neck band in the present embodiment, however, it may have a structure called a headset, a headband, or the like.

The connector 3 incorporates a bone conduction wave generation device 10 (see FIG. 2) described later, in addition to a power source such as a cell and a battery.

According to the present embodiment, the bone conduction wave output apparatus 1 includes the bone conduction wave generation device 10 described later, however, is not limited to the structure incorporating the bone conduction wave generation device 10.

That is to say, the bone conduction wave generation device 10 may be included not in the bone conduction wave output apparatus 1 but in an external device (for example, a smartphone, a tablet terminal, and the like), and the bone conduction wave output apparatus 1 include a power source such as a cell or a battery and the output unit 2.

In such a case, at a receiving port, the bone conduction wave output apparatus 1 receives a first output wave and a second output wave for bone conduction described later, which are generated by the bone conduction wave generation device 10 provided in the external device, or a signal having a frequency in an inaudible range which is made by, for example, encoding of the first output wave and the second output wave. From the first output unit 2a and the second output unit 2b of the output unit 2, the bone conduction wave output apparatus 1 outputs a bone conduction wave depending on the first output wave and the second output wave obtained by processing such as decoding as needed.

(Bone Conduction Wave Generation Device 10)

Figure 2:
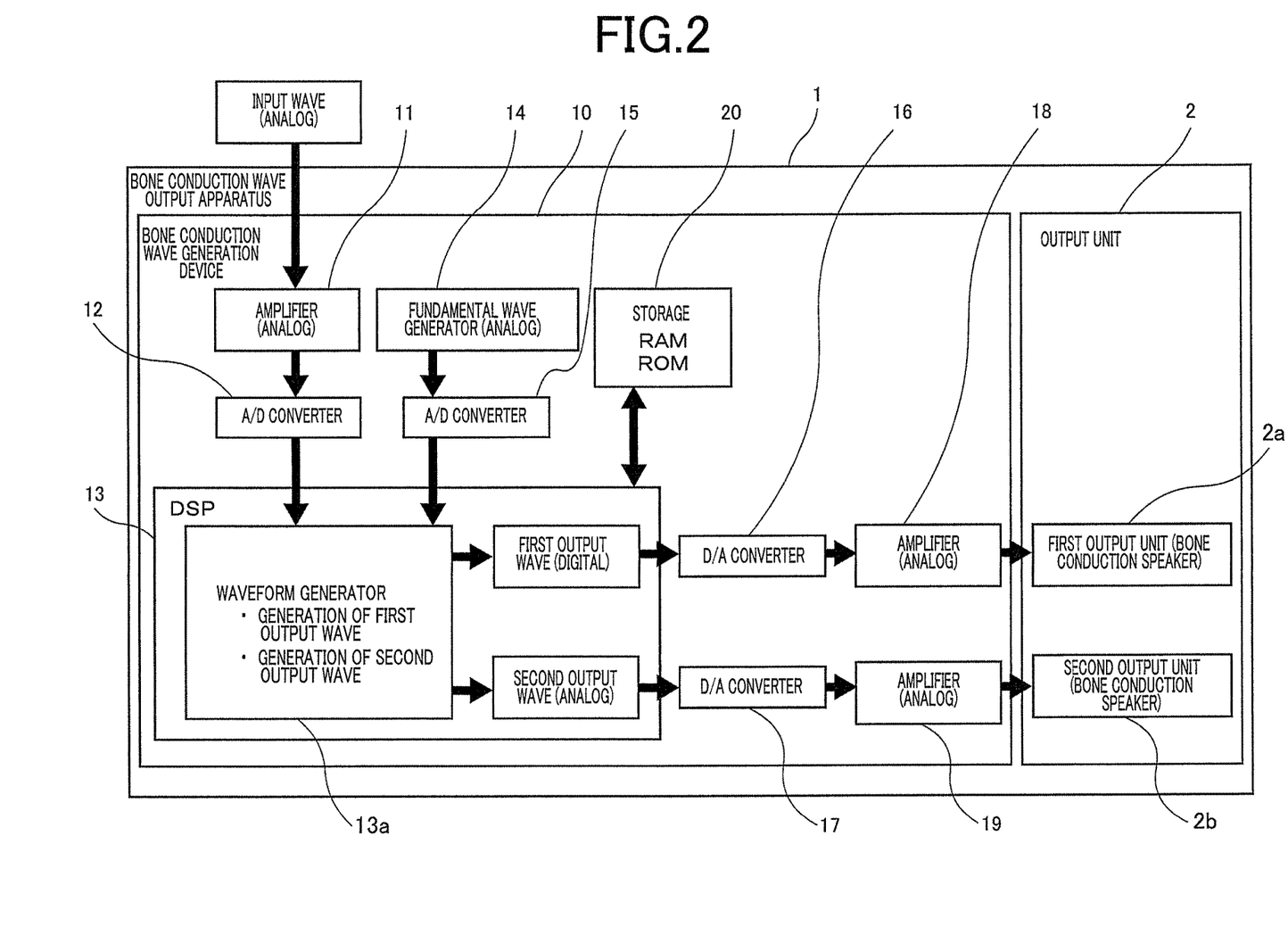
FIG. 2 is a block diagram of the bone conduction wave output apparatus according to an embodiment of the present invention.

FIG. 2 is a block diagram of the bone conduction wave output apparatus 1.

As shown in FIG. 2, the bone conduction wave generation device 10 includes an analog amplifier 11 to amplify the analog input wave from outside, an A/D converter 12 (analog/digital converter) to convert the amplified analog input wave into a digital signal, and a waveform generator 13a to perform calculation to generate the first output wave and the second output wave described later on the basis of the input wave after digital conversion.

If the sound signal for bone conduction which corresponds to the input wave and is input from the outside is a digital signal, the bone conduction wave generation device 10 does not need to include the A/D converter 12. If the sound signal for bone conduction has been encoded at the time of input, the bone conduction wave generation device 10 incorporates a decoder to perform decode processing.

DSP 13 (digital signal processor) which processes a signal is formed, for example, to partly function as the waveform generator 13a. Except for the function as the waveform generator 13a, the DSP 13 also performs overall control of the bone conduction wave generation device 10.

Furthermore, the bone conduction wave generation device 10 includes a fundamental wave generator 14 which generates a first fundamental wave to form the first output wave and a second fundamental wave to form the second output wave, an A/D converter 15 (analog/digital converter) which converts the analog fundamental wave generated by the fundamental wave generator 14 into a digital signal, a D/A converter 16 (digital/analog converter) which converts the digital first output wave generated by the waveform generator 13a into an analog first output wave, and a D/A converter 17 (digital/analog converter) which converts the digital second output wave generated by the waveform generator 13a into an analog second output wave.

If the fundamental wave generator 14 generates a digital signal as the fundamental wave, the A/D converter 15 is not required.

Furthermore, the bone conduction wave generation device 10 includes an analog amplifier 18 which amplifies the analog first output wave output from the D/A converter 16 before transfer to the first output unit 2a, an analog amplifier 19 which amplifies the analog second output wave output from the D/A converter 17 before transfer to the second output unit 2b, and a storage 20 which stores various programs executed by the DSP 13, data, and the like.

The storage 20 includes, for example, a RAM as a storage portion which can be freely read and write and a ROM as a storage portion which can be read only. The ROM stores various programs to be executed by the DSP 13, data tables, and the like.

The RAM not only stores data required by the DSP 13 to execute various programs, but also functions as a temporary storage which temporarily loads the programs, stores the input wave, and stores data generated in the processing where the DSP 13 executes various programs (such as the first output wave and the second output wave described later).

The DSP 13 may partly or entirely incorporate the RAM, ROM, and the like of the storage 20 for acceleration.

(Outline of Processing by Waveform Generator 13a)

Figure 3A:
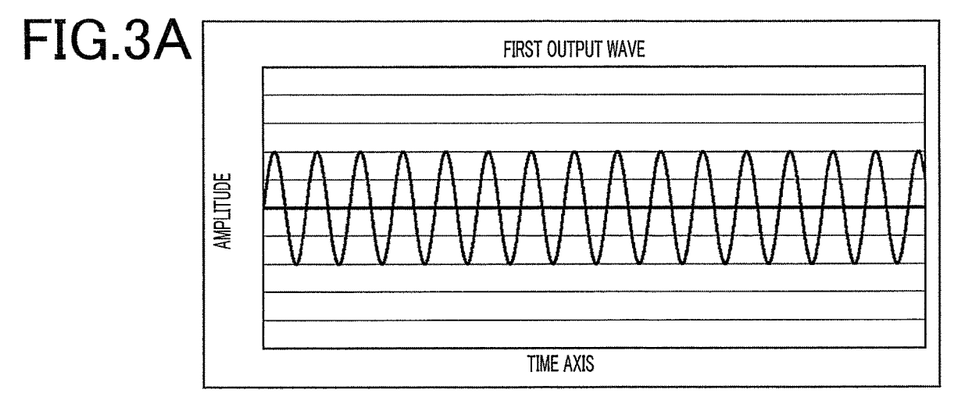
FIG. 3A is a diagram showing a first output wave to explain outlines of processing performed by a waveform generator according to an embodiment of the present invention.
Figure 3B:
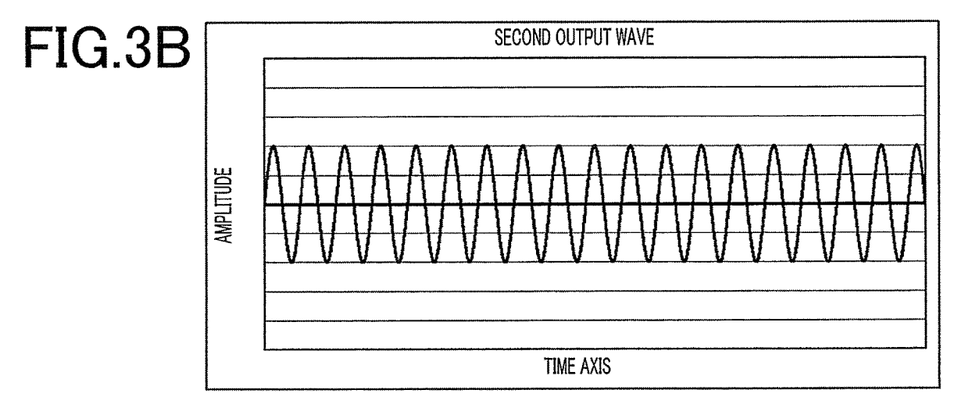
FIG. 3B is a diagram showing a second output wave to explain outlines of processing performed by the waveform generator according to an embodiment of the present invention.
Figure 3C:
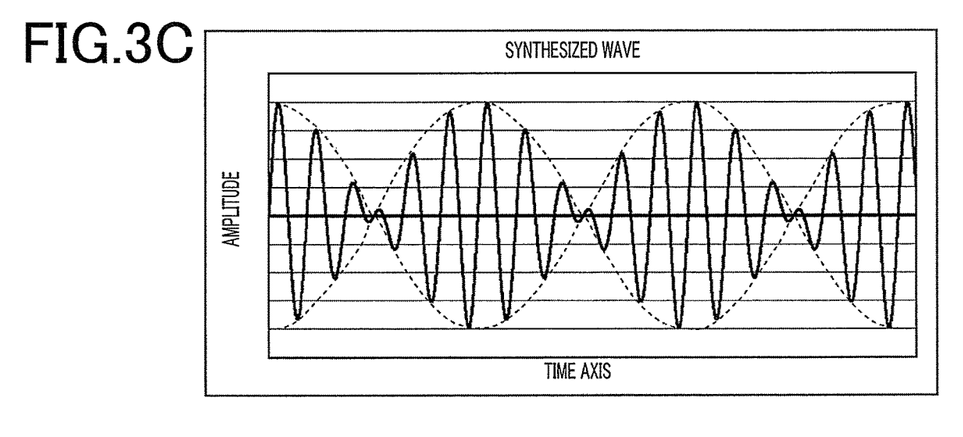
FIG. 3C is a diagram showing a composite wave obtained by combining the first output wave and the second output wave to explain outlines of processing performed by the waveform generator according to an embodiment of the present invention.

FIGS. 3A to 3C are diagrams to explain outlines of processing by the waveform generator 13a. FIG. 3A is a diagram showing the first output wave, FIG. 3B a diagram showing the second output wave, and FIG. 3C is a diagram showing a composite wave obtained by combining the first output wave and the second output wave.

In FIGS. 3A to 3C, a time axis (may be regarded as a phase axis) is respectively shown on a horizontal axis and an amplitude is shown on a vertical axis. Horizontal minor grid lines representing the amplitude are drawn at an interval common to all the drawings.

The waveform generator 13a generates the first output wave and the second output wave as in FIG. 3A and FIG. 3B by a method described later for generating the first output wave and the second output wave.

The frequency of the first output wave is, for example, 50 kHz or more, and the frequency of the second output wave is also, for example, 50 kHz or more.

Because it is generally said that frequency of an audible sound wave by a man with ears is from 20 Hz to 20 kHz, the first output wave and the second output wave are outside of an audible range by a man with ears.

Furthermore, the first output wave is different from the second output wave in phase or frequency. Therefore, if these two waves are output from the first output unit 2a and the second output unit 2b of the output unit 2 and bone conduction is started, the waves are combined into the composite wave shown in FIG. 3C.

Here, while the frequency of the first output wave is 50 kHz, for example, the second output wave is subjected to an angular modulation (for example, a phase modulation or a frequency modulation) within a frequency range of 20 kHz or less based on 50 kHz.

As a result of combining the waves, the amplitude of the first output wave increases or decrease as in FIG. 3C due to the second output wave.

The first output wave is explained as a reference in the following explanation, however, it is not important whether the reference wave is the first wave or the second wave, because FIG. 3C can also be explained that the amplitude of the second output wave increases or decreases due to the first output wave.

As a result, the composite wave shown in FIG. 3C also has a property of waves having an envelope indicated by dotted lines.

This envelope provides a beat having a frequency corresponding to the frequency difference between the first output wave and the second output wave. If the beat has a frequency within the audible range, a man recognizes a sound corresponding to the beat with ears.

Specifically, if the shape of the envelope of the composite wave is similar to or the same as the shape of the input wave, a man recognizes a sound having characteristics similar to or the same as the input wave with ears.

That is to say, if the first output wave and the second output wave are generated as waves equal to or larger than 20 kHz, the audible range by a man, a man does not recognize the first output wave and the second output wave in themselves with ears. However, if the frequency difference between the first output wave and the second output wave generated by the waveform generator 13a is 20 kHz or less so that the beat of the composite wave is recognized as the sound similar to the input wave, a man who heard the beat recognizes as if the output unit 2 outputs the input wave as a sound wave of the audible range.

Furthermore, as described above, if the frequency of the first output wave is 50 kHz and the second output wave is subjected to an angular modulation (for example, a phase modulation or a frequency modulation) within a frequency range of 20 kHz or less based on 50 kHz, the frequency difference is 20 kHz or less. Therefore, the composite wave formed by combining the first output wave and the second output wave has an audible beat by a man.

Because the first output unit 2a and the second output unit 2b are fixed on the head H of a man, they are at a fixed distance from the portion for auditory perception. Accordingly, a desired composite wave can be always recognized whether the head H is moved or not.

Here, the first output wave and the second output wave leak from the first output unit 2a and the second output unit 2b in directions other than the direction toward the man wearing the bone conduction wave output apparatus 1. It is significantly difficult to combine the leaking waves because the propagation is not through bones which easily propagate waves, but through air.

Therefore, it is difficult to recognize the first output wave and the second output wave leaked outside as sound. This results in high confidentiality and suppresses discomfort given to surrounding people.

Furthermore, because the range (distance) for overlapping high frequency waves as desired is small (short), if the frequency is about 50 kHz and the surrounding people moves in the order of several centimeters or several millimeters relative to the first output unit 2a and the second output unit 2b, for example, the beat of the composite wave is disturbed and is difficult to be heard as sound of the audible range.

In particular, disturbance of the beat is more complicated by combining with wave of surrounding environmental sound.

Actually, a man is not in a completely stationary state even while intending to be in a stationary state. Accordingly, even if the waves can be recognized as a sound at a moment, it would be difficult to understand the contents.

Furthermore, a generally used bone conduction speaker generates a wave within audible range at a high output power as a wave to be conducted through bones for performing bone conduction. As a result, the sound leaks from the bone conduction speaker at a large sound pressure level and thereby makes the surrounding people uncomfortable.

Meanwhile, according to the present embodiment described above, it is difficult to form the composite wave (hereinafter, also referred to as a leaking composite wave) by combining the first output wave and the second output wave which leak to the surroundings. Thus, unlike the wave propagated by bones, the leaking composite wave has a low sound pressure level in itself and hardly makes the surrounding people uncomfortable.

Considering leakage of the composite wave by combination in bones, the wave propagated by skins etc., which hardly propagates waves, is significantly reduced, so that the wave would hardly be recognized as sound.

(Specific Example of Processing in Waveform Generator 13a)

An example of generation of the first output wave and the second output wave as described above is explained in detail.

It should be noted that the specific example to be explained below is merely an example and, as described later, does not the limit the present invention.

First of all, in accordance with the general description of waves, the waveform f(t) of the first output wave is defined to be represented by the following equation (1) and the waveform g(t) of the second output wave to be represented by the following equation (2).

$$f(t) = Af \times \cos(w \times t + \varphi c) \quad (1)$$

$$g(t) = Ag \times \cos(w \times t + \varphi c + (t)) \quad (2)$$

Here, w represents an angular frequency and satisfies $w = 2 \times \pi \times fc$ (fc is a frequency). Even if the frequency of the second output wave g(t) is different from the frequency of the first output wave f(t) by around 20 kHz at the maximum, for example, the frequency fc is set to be not less than 20 kHz, which is the highest frequency in the audible range.

For example, fc is set to be 40 kHz or more, more preferably 50 kHz or more.

Af and Ag represent an amplitude which is a fixed value (Af may be equal to or different from Ag), that is, a constant given firstly and appropriately.

Furthermore, φc represents an initial phase and is the same value in f(t) and g(t).

Comparison of the equations (1) and (2) described above reveals that the first output wave f(t) and the second output wave g(t) are basically similar to each other, however, the second output wave g(t) is angularly modulated (in the present example, modulated in phase) by the function φ(t) for phase modulation.

In the following explanation, the phase modulation is used as the example of the angular modulation, however, the frequency modulation can be also used as an example of the phase modulation. Accordingly, the second output wave g(t) is not limited to a wave modulated in phase but in frequency.

If the input wave from the outside is defined as s(t), the first output wave f(t) and the second output wave g(t) to be generated are to be defined, as described above, such that an envelope of the composite wave p(t) of them has a shape similar to or the same as the waveform of the input wave s(t).

Therefore, after the composite wave p(t) having an envelope having a shape similar to or equal to the waveform of the target input wave s(t) is found, f(t) and g(t) satisfying p(t)=f(t)+g(t) are defined.

Regarding the f(t) and g(t), the amplitudes Af and Ag are initially defined to be a constant which satisfies a certain condition described later. The initial phase φc is also predetermined. Furthermore, the fc is also pre-selected to be a frequency which is sure to be outside of the audible range. Accordingly, in order to obtain the composite wave p(t) having a desired envelope, only the function φ(t) for phase modulation of g(t) is required to be found and adjusted depending on the input wave s(t).

The target composite wave p(t) shown in FIG. 3C can be obtained by modulating the amplitude Af of the first input wave f(t) by the input wave s(t).

Accordingly, if p(t) is the first input wave f(t) subjected to amplitude modulation by the input wave s(t) in accordance with the general description of amplitude modulation, the p(t) can be described by the following equation (3).

$$p(t)=Af\times[1+s(t)]\times\cos(w\times t+\varphi c) \quad (3)$$

Because the f(t) and g(t) are required to be combined such that the amplitude of p(t) can be Af×[1+s(t)], the amplitude Af of the f(t) and the amplitude Ag of the g(t) are defined such that Af×[1+s(t)]≤Af+Ag is satisfied.

As described above, it is necessary to obtain φ(t) so that p(t)=f(t)+g(t) is satisfied. By substitution of the above equations (1), (2), and (3) into this equation and deleting the terms common to the right side and the left side, the left side is represented by the following equation (4-1) and the right side is represented by the following equation (4-2):

$$(\text{left side})=Af\times s(t)\times\cos(w\times t+\varphi c) \quad (4-1)$$

$$(\text{right side})=Ag\times\cos(w\times t+\varphi c+\varphi(t)) \quad (4-2)$$

Here, if w×t+φc is represented to be z, t can be represented to be t=[(z−φc)/w].

The following equation (5) can be obtained by representing [(z−φc)/w] to be a symbol u in order to avoid confusion with t and substituting the symbol u in the equations (4-1) and (4-2).

$$Af\times s(u)\times\cos(z)=Ag\times\cos(z+\varphi(u)) \quad (5)$$

Here, in accordance with the Euler formula, cos(z) and cos(z+φ(u)) can be represented by exponential functions $e^{iz}$ and $e^{i(z+\varphi(u))}$.

Specifically, cos(z) is equivalent to $[e^{iz}+e^{-iz}]/2$ and cos(z+φ(u)) is equivalent to $[e^{i(z+\varphi(u))}+e^{-i(z+\varphi(u))}]/2$.

Here, "i" means an imaginary unit ($i^2=-1$).

Accordingly, by representing the term as to "cos" with an exponential function for arrangement of equation, the following equation (6) can be obtained.

$$[Af\times s(u)-Ag\times e^{i\varphi(u)}]\times e^{iz}+[Af\times s(u)-Ag\times e^{-i\varphi(u)}]\times e^{-iz}=0 \quad (6)$$

Here, if z=0 is satisfied, the exponential functions $e^{iz}$ and $e^{-iz}$ are both "$e^0$", which is "1".

Furthermore, because u is defined to be a symbol which represents [(z−φc)/w], u satisfies u=[(0−φc)/w]=−[(φc/w] if z=0 is satisfied.

Therefore, by substituting "z=0" and "u=−[φc/w]" in the equation (6) and by arranging common terms, equation (7) can be obtained.

$$2\times Af\times s(-\varphi c/w)-Ag\times[e^{i\varphi(-\varphi c/w)}+e^{-i\varphi(-\varphi c/w)}]=0 \quad (7)$$

Equation (8) is obtained by division of both sides by 2.

$$Af\times s(-\varphi c/w)-Ag\times\{[e^{i\varphi(-\varphi c/w)}+e^{-i\varphi(-\varphi c/w)}]/2\}=0 \quad (8)$$

Here, because "u" is just a substitution of "t", when z=0, t also satisfies t=−[(φc/w] and −φc=w×t. By substituting w×t for −φc in the equation (8), equation (9) can be obtained.

$$Af\times s(t)-Ag\times\{[e^{i\varphi(t)}+e^{-i\varphi(t)}]/2\}=0 \quad (9)$$

In accordance with the Euler formula again, the terms of exponential function in { } in the equation (9) can be returned to terms using "cos" so as to obtain the following equation (10).

$$Af\times s(t)-Ag\times\cos(\varphi(t))=0 \quad (10)$$

Accordingly, by transformation of the equation (10), φ(t) is obtained as in the following equation (11).

$$\varphi(t)=\arccos[(Af/Ag)\times s(t)] \quad (11)$$

That is, the first output unit 2a outputs the first output wave represented by f(t)=Af×cos(w×t+φc) and the second output unit 2b outputs the second output wave represented by g(t)=Ag×cos(w×t+φc+φ(t)) obtained by phase modulation using φ(t) represented by the input wave s(t) according to the equation (11).

It should be noted that the above description is merely an example and does not limit the present invention.

For example, in the storage 20 may be prepared a table including a lot of combinations of the first output wave and the second output wave corresponding to sounds considered to be included in the input wave s(t). The waveform generator 13a may select a suitable combination from the prepared table of the first output wave and the second output wave on the basis of the input wave s(t) so as to generate the first output wave and the second output wave on the basis of the input wave s(t).

In the above explanation, the first fundamental wave is not modulated at all to form the first output wave f(t) but used as the first output wave f(t) in itself, however, the first output wave f(t) may be also angularly modulated (modulated in phase or in frequency). Alternatively, the first output wave f(t) may be the first fundamental wave subjected to angular modulation and the second output wave g(t) may be the second fundamental wave itself.

Furthermore, it is not necessary that the first output wave f(t) and the second output wave g(t) are respectively formed from one first fundamental wave and one second fundamental wave as in the present embodiment. For example, multiple fundamental waves having a frequency fc different from each other are prepared so that the fundamental wave to be used can be changed depending on the input wave s(t).

Thus, it should be noted that the above example is merely an example.

Figure 4:
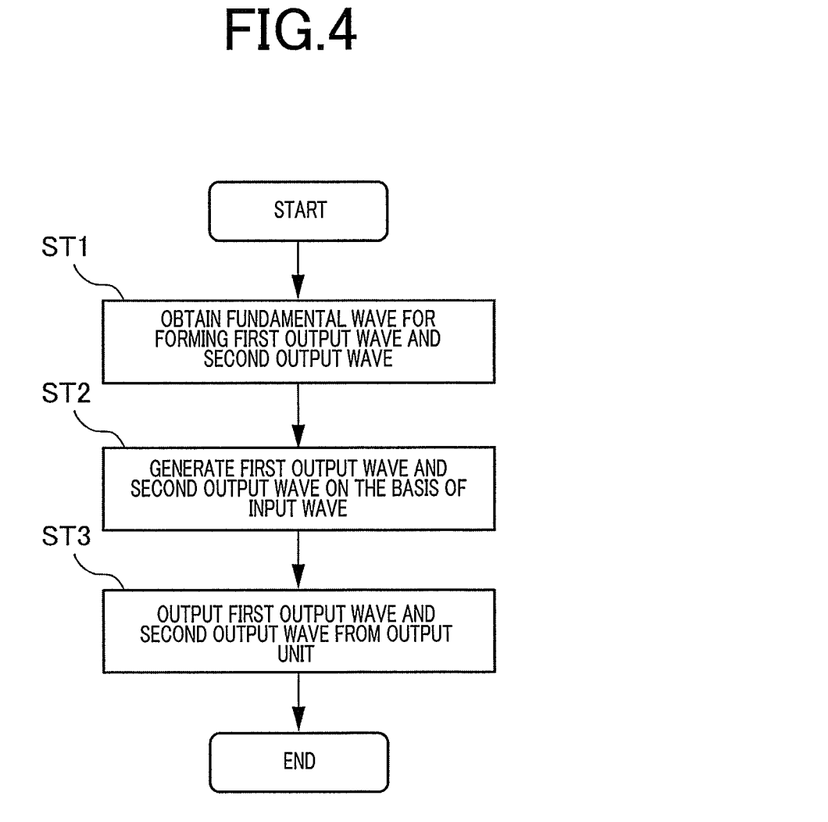
FIG. 4 is a flowchart showing processing performed by the waveform generator according to an embodiment of the present invention.

Next, the operation of the waveform generator 13a is confirmed in reference to the flowchart in FIG. 4 showing processing executed by the waveform generator 13a.

When the input wave s(t) is input into the bone conduction wave output apparatus 1, the processing described in the flowchart in FIG. 4 is started. The input wave s(t) includes sound from an external device (such as a smart phone, a tablet terminal, and a portable digital music player), an analog wave of voice, or a digital wave prepared by digital processing of this analog wave.

When the flow is started, in step ST1, the waveform generator 13a obtains the first fundamental wave and the second fundamental wave to form the first output wave f(t) and the second output wave g(t) from the fundamental wave generator 14.

In the above example, both of the first fundamental wave and the second fundamental wave are f(t).

Next, in step ST2, the waveform generator 13a generates the first output wave f(t) outside of the audible range and the second output wave g(t) outside of the audible range on the basis of the input wave s(t). A composite wave p(t) having an audible beat can be provided if the first output wave f(t) and the second output wave g(t) are combined.

Specifically, in the above example, the function $\varphi(t)$ is calculated on the basis of the input wave s(t) and is used for phase modulation of the second fundamental wave so that the second output wave g(t) is formed depending on the input wave s(t). The first fundamental wave itself is used as the first output wave f(t), and the second fundamental wave (in the above example, the same wave as the first fundamental wave) is used as the second output wave g(t) after phase modulation by the function $\varphi(t)$.

Because the first output wave f(t) and the second output wave g(t) have constant amplitudes Af and Ag as described above, no beat occurs if they are individually heard. Meanwhile, the first output wave f(t) and the second output wave g(t) are generated such that a composite wave p(t) obtained by combining the first output wave f(t) and the second output wave g(t) has an envelope similar to the input wave s(t).

Furthermore, because the function $\varphi(t)$ is formed for phase modulation based on the input wave s(t) in an audible frequency band (audible range) with ears, even if the generated first output wave f(t) and the second output wave g(t) have a frequency of more than 20 kHz, the generated first output wave f(t) and the second output wave g(t) are different by the frequency of 20 kHz or less and are combined into the composite wave having an audible beat provided by combining the first output wave f(t) and the second output wave g(t).

In the step ST3, the first output wave f(t) and the second output wave g(t) generated as above are transferred to the first output unit 2a and the second output unit 2b by the waveform generator 13a and output by the first output unit 2a and the second output unit 2b to the outside as bone conduction waves. The series of processing is thereby completed.

The first output wave f(t) and the second output wave g(t) for bone conduction are output in this way and form a composite wave in a bone of a user. The user hears the beat of the composite wave p(t) and feels as if the input wave s(t) has been transferred as a sound wave.

Thus, the bone conduction wave output apparatus 1 according to the present invention is explained on the basis of the specific embodiment, however, the present invention is not limited to the specific embodiment described above.

For example, according to the above embodiment, as illustrated in the block diagram of FIG. 2, the DSP 13 is partly used as the waveform generator 13a.

Alternatively, an analog modulation circuit which processes an analog wave as it is may be used as the waveform generator 13a.

In such a case, the analog modulation circuit may be used as the portion described as DSP 13 in FIG. 2, and the A/D converters 12 and 15 and the D/A converters 16 and 17 may be omitted.

Even in such a case, the DSP 13 in itself is incorporated in the bone conduction wave generation device 10 as a controller which entirely controls the processing by the bone conduction wave generation device 10.

Furthermore, as mentioned above, in the storage 20 may be prepared a table including combinations of the first output wave f(t) and the second output wave g(t) corresponding to sound and thereby a suitable combination of the first output wave f(t) and the second output wave g(t) can be selected from the table depending on the input wave s(t), so that the first output wave f(t) and the second output wave g(t) are generated on the basis of the input wave s(t).

Specifically, if a waveform of the input wave s (t) corresponds to a conversation voice sent from a smartphone to the bone conduction wave output apparatus 1, for example, the bone conduction wave generation device 10 generates the first output wave f(t) and the second output wave g(t) corresponding to the conversation voice.

Thus, in the storage 20 are prestored combinations corresponding to voices used in conversations, such as a combination of the first output wave f(t) and the second output wave g(t) corresponding to the sound "a", the first output wave f(t) and the second output wave g(t) corresponding to the sound "i", and the like.

The number of combinations of the first output wave f(t) and the second output wave g(t) corresponding to "a" is not need to be one, because the pronunciation of the same sound "a" varies from person to person. Some pronounce "a" in a high tone, others pronounce "a" in a low tone. Therefore, preferably, combinations of the first output wave f(t) and the second output wave g(t) are prepared individually corresponding to "a" from a high tone to a low tone.

The input wave s(t) corresponding to the voice is then transferred from the smartphone to the bone conduction wave output apparatus 1 and is input to the bone conduction wave generation device 10. The bone conduction wave generation device 10 performs voice analysis of the input wave s(t) in accordance with an audio analysis program and, corresponding to the voice obtained by the voice analysis, selects a suitable combination of the first output wave f(t) and the second output wave g(t) from the table stored in the storage 20. The first output wave f(t) and the second output wave g(t) based on the input wave s(t) are thereby generated.

In the above embodiment, a pair of the first output unit 2a and the second output unit 2b is provided as the bone conduction wave output apparatus 1 respectively for the left ear and for the right ear, however, a pair of the first output unit 2a and the second output unit 2b may be provided for only one of the ears.

In the case of both (left and right) ears, the input wave s(t) includes an input wave sl(t) for the left ear and an input wave sr(t) for the right ear. The input wave sl(t) for the left ear and the input wave sr(t) for the right ear may have different waveforms or may have the same waveform. In the case of one (left or right) ear, the input wave s(t) includes an input wave for the one ear only.

If the input wave s(t) is for both (left and right) ears as in the embodiment described above, the waveform generator 13a generates a first output wave fl(t) and a second output wave gl(t) corresponding to the input wave sl(t) for the left ear and a first output wave fr(t) and a second output wave gr(t) corresponding to the input wave sr(t) for the right ear.

That is, according to the above embodiment, the first output wave fl(t) for the left ear and the first output wave fr(t) for the right ear are collectively referred to as the first output wave f(t), and the second output wave gl(t) for the left ear and the second output wave gr(t) for the right ear are collectively referred to as the second output wave g(t).

If the input wave s(t) is for one ear, the waveform generator 13a generates the first output wave f(t) and the second output wave g(t) for only one ear.

The bone conduction wave generation device 10 or the DSP 13 may have a determination unit which determines whether the input wave s(t) is for only one ear or for both ears, so that the first output wave f(t) and the second output wave g(t) can be suitably generated in accordance with the determination by the determination unit.

Needless to say, the combinations of the first output wave f(t) and the second output wave g(t) stored in the storage 20 are not limited to combinations corresponding to voices, but may be combinations corresponding to instrumental sounds for listening to music, for example.

The frequency of the first output wave f(t) and the second output wave g(t) have only to be outside of the audible frequency range. The frequency is not limited to be higher than the audible frequency range as described above but may be lower than the audible frequency range, however, the frequency higher than the audible frequency is more preferred for output at a speed corresponding to the input wave s(t).

Although some embodiments of the present invention have been explained, these embodiments are shown as examples and do not construed to limit the scope of the invention. These embodiments can be carried out in various other embodiments, and various omissions, substitutions, and changes can be made without departing from the gist of the invention. These embodiments and modifications thereof are included in the scope of the invention recited in the claims and their equivalents, as well as the scope and gist of the invention.

The entire disclosure of Japanese patent application No. 2016-182120, filed on Sep. 16, 2016, is incorporated in the specification by reference in its entirety.

INDUSTRIAL APPLICABILITY

The present invention can be applied in the field of a bone conduction wave generation device and a bone conduction wave output apparatus.

DESCRIPTION OF REFERENCE NUMERALS

1 bone conduction wave output apparatus
2 output unit
2A first output unit
2b second output unit
3 connector
10 bone conduction wave generation device
11, 18, 19 analog amplifier
12, 15 A/D converter
13 DSP
13a waveform generator
14 fundamental wave generator
16, 17 D/A converter
20 storage
H head

The invention claimed is:

1. A bone conduction wave output apparatus comprising:
   a waveform generator which generates a first output wave and a second output wave for bone conduction, wherein the waveform generator generates, on a basis of an input wave, the first output wave outside of an audible range and the second output wave outside of an audible range which are to be combined into a composite wave having an audible beat;
   a first output unit which contacts a first area adjacent to one ear and outputs the first output wave for the first area; and
   a second output unit which contacts a second area different from the first area and outputs the second output wave for the second area such that the composite wave is generated in the one ear.

2. The bone conduction wave output apparatus according to claim 1, wherein the waveform generator performs angular modulation of at least one of a first fundamental wave to form the first output wave and a second fundamental wave to form the second output wave.

3. The bone conduction wave output apparatus according to claim 2, wherein the angular modulation is a phase modulation.

4. The bone conduction wave output apparatus according to claim 2, wherein the waveform generator uses the first fundamental wave and the second fundamental wave which have a frequency outside of an audible range.

5. The bone conduction wave output apparatus according to claim 1, wherein the waveform generator generates the first output wave and the second output wave such that a waveform of an envelope of the composite wave is similar to or same as a waveform of the input wave.

6. The bone conduction wave output apparatus according to claim 1, wherein the waveform generator generates a first output wave and a second output wave which have a constant amplitude.

7. The bone conduction wave output apparatus according to claim 1, wherein the waveform generator generates the first output wave and the second output wave which have a frequency outside of an audible range.

8. The bone conduction wave output apparatus according to claim 1, wherein the waveform generator generates the first output wave and the second output wave such that a difference in frequency between the first output wave and the second output wave is within an audible range.

9. A bone conduction wave generation method comprising:
   generating, on a basis of an input wave, a first output wave outside of an audible range and a second output wave outside of an audible range for bone conduction which are to be combined into a composite wave having an audible beat;
   outputting, via a first output unit which contacts a first area adjacent to one ear, the first output wave for the first area; and
   outputting, via a second output unit which contacts a second area different from the first area, the second output wave for the second area such that the composite wave is generated in the one ear.

10. A non-transitory recording medium storing a computer readable program for a bone conduction wave output apparatus, the program causing the bone conduction wave output apparatus to perform functions comprising:
- generating, on a basis of an input wave, a first output wave outside of an audible range and a second output wave outside of an audible range for bone conduction, wherein the first output wave and the second output wave are to be combined into a composite wave having an audible beat;
- outputting, via a first output unit which contacts a first area adjacent to one ear, the first output wave for the first area; and
- outputting, via a second output unit which contacts a second area different from the first area, the second output wave for the second area such that the composite wave is generated in the one ear.

* * * * *